(12) United States Patent
Minoux et al.

(10) Patent No.: US 9,000,236 B2
(45) Date of Patent: Apr. 7, 2015

(54) PURIFICATION OF ALCOHOLS PRIOR TO THEIR USE IN THE PRESENCE OF AN ACID CATALYST

(75) Inventors: Delphine Minoux, Familleureux (BE); Walter Vermeiren, Houthalen (BE); Nikolai Nesterenko, Nivelles (BE); Sander Van Donk, Uccle (BE); Jean-Pierre Dath, Beloeil Hainault (BE)

(73) Assignee: Total Research & Technology Feluy, Seneffe (Feluy) (BE)

( * ) Notice: Subject to any disclaimer, the term of this patent is extended or adjusted under 35 U.S.C. 154(b) by 886 days.

(21) Appl. No.: 13/131,407

(22) PCT Filed: Nov. 27, 2009

(86) PCT No.: PCT/EP2009/065951
§ 371 (c)(1),
(2), (4) Date: Sep. 7, 2011

(87) PCT Pub. No.: WO2010/060981
PCT Pub. Date: Jun. 3, 2010

(65) Prior Publication Data
US 2011/0313213 A1    Dec. 22, 2011

(30) Foreign Application Priority Data
Nov. 28, 2008 (EP) .................................. 08170254
May 15, 2009 (EP) .................................. 09160435

(51) Int. Cl.
| | | |
|---|---|---|
| C07C 29/74 | (2006.01) | |
| C07C 1/24 | (2006.01) | |
| C07C 29/76 | (2006.01) | |
| C07C 29/90 | (2006.01) | |

(52) U.S. Cl.
CPC . *C07C 1/24* (2013.01); *C07C 29/76* (2013.01); *C07C 29/90* (2013.01)

(58) Field of Classification Search
CPC ........ C07C 29/74; C07C 29/76; C07C 29/88; C07C 31/08
USPC .................................................. 568/913, 914
See application file for complete search history.

(56) References Cited

U.S. PATENT DOCUMENTS

| | | |
|---|---|---|
| 4,207,424 A | 6/1980 | Winnick |
| 6,538,168 B1 | 3/2003 | Schwab et al. |
| 6,770,790 B1 | 8/2004 | Li et al. |
| 2007/0167530 A1 | 7/2007 | Gerlach et al. |

FOREIGN PATENT DOCUMENTS

| | | |
|---|---|---|
| EP | 1176132 A1 | 1/2002 |
| JP | 56-083427 A | 7/1981 |
| JP | 04-338349 A | 11/1992 |

OTHER PUBLICATIONS

Office Action issued in Japanese Application No. 2011-537985 mailed Apr. 23, 2013, and an English translation thereof (5 pages).
Office Action issued in Japanese Application No. 2011-537985 mailed Mar. 4, 2014, and an English translation thereof (6 pages).
Office Action issued in Korean Application No. 2011-7012160 mailed Oct. 30, 2013, and an English translation thereof (14 pages).

*Primary Examiner* — Elvis O Price

(57) ABSTRACT

Process for the purification of an alcohol in the course of a process comprising:
(1) providing a reaction zone (C) comprising an acid type catalyst;
(2) providing a reaction zone (B) comprising an acid adsorbent material;
(3) providing an alcohol stream comprising impurities;
(4) introducing the alcohol stream of (3) into the reaction zone (B) and bringing said stream into contact with the acid adsorbent material at conditions effective to reduce the amount of impurities having an adverse effect on the acid type catalyst of the reaction zone (C);
(5) recovering from step (4) an alcohol stream and introducing it into the reaction zone (C);
(6) optionally introducing one or more reactants (R) into the reaction zone (C);
(7) operating said reaction zone (C) at conditions effective to recover a valuable effluent.

15 Claims, 3 Drawing Sheets

Figure 1:
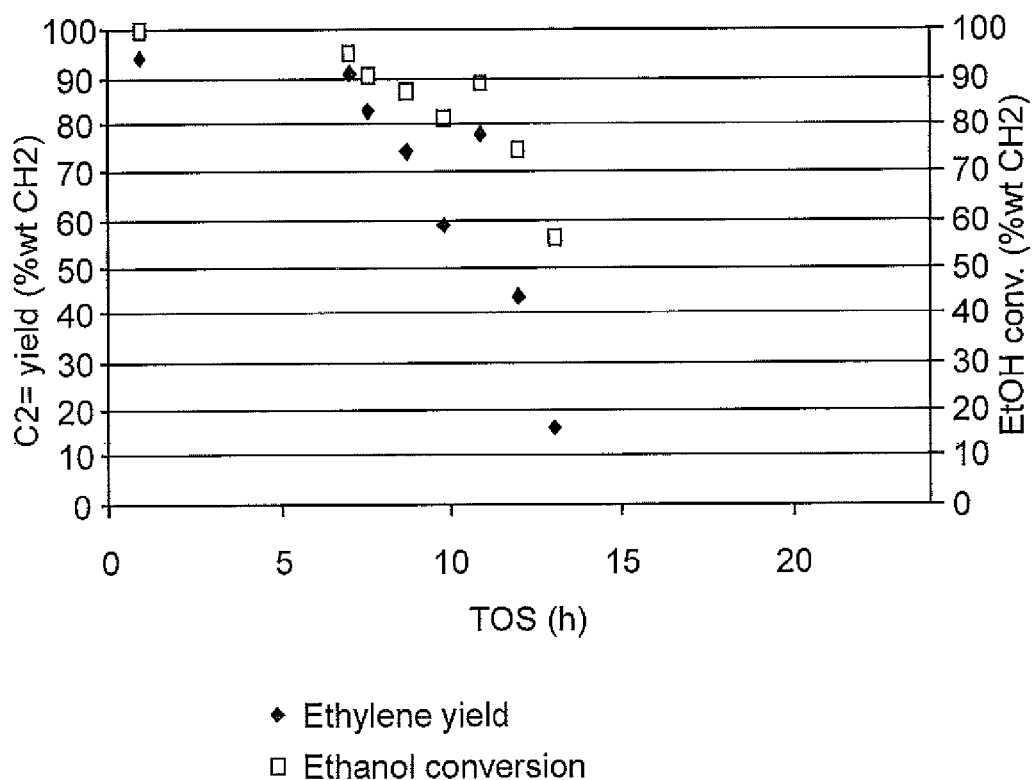

- ◆ C2= Selectivity
- □ C2= Purity

- ◆ C2 yield
- □ Ethanol conversion

PURIFICATION OF ALCOHOLS PRIOR TO THEIR USE IN THE PRESENCE OF AN ACID CATALYST

CROSS-REFERENCE TO RELATED APPLICATIONS

This application claims the benefit of PCT/EP2009/065951, filed Nov. 27, 2009, which claims priority from EP 08170254.0, filed Nov. 28, 2008 and EP 09160435.5, filed May 15, 2009.

FIELD OF THE INVENTION

The present invention relates to the purification of alcohols prior to their use in the presence of an acid catalyst. Such use is e.g. the etherification of isobutene and isoamylenes by ethanol to make ETBE and ETAE, the self-etherification or the dehydration of alcohols to make olefins. The limited supply and increasing cost of crude oil has prompted the search for alternative processes for producing hydrocarbon products such fuels and such as ethylene. Ethanol can be obtained by fermentation of carbohydrates. Made up of organic matter from living organisms, biomass is the world's leading renewable energy source. The dehydration is made in the presence of a catalyst such as alumina or silica-alumina. Such process works well with a substantially pure ethanol such as an ethanol coming from a distillation step or dewatering over molecular sieves by adsorption, but said distillation step or adsorption step requires a lot of energy. On the other hand the use of a raw ethanol leads to a poisoning of acidic catalyst. The present invention relates in one embodiment to a purification process of the raw alcohol which doesn't requires a lot of energy and prevents the poisoning of an acid catalyst.

BACKGROUND OF THE INVENTION

The dehydration of alcohols has been described in a lot of prior arts. U.S. Pat. No. 4,207,424 describes a process for the catalytic dehydration of alcohols to form unsaturated organic compounds in which an alcohol is dehydrated in the presence of alumina catalysts which are pre-treated with an organic silylating agent at elevated temperature. U.S. Pat. No. 4,302,357 relates to an activated alumina catalyst employed in a process for the production of ethylene from ethanol through a dehydration reaction. In the description, LHSV of ethanol is from 0.25 to 5 h$^{-1}$ and preferably from 0.5 to 3 h$^{-1}$. The examples are carried out at 370° C. and LHSV of 1 h$^{-1}$, ethylene yield is from 65 to 94%. U.S. Pat. No. 4,232,179 relates to the preparation of ethylene, based on a process for dehydrating ethyl alcohol. More particularly, the object of said prior art is the production of ethylene in the presence of catalysts, using adiabatic reactors and a high temperature. Such adiabatic reactors may be used in parallel or may be arranged in series or arranged in assemblies of parallel series, or still only a single reactor may be used. EP 22640 relates to improved zeolite catalysts, to methods of producing such catalysts, and to their use in the conversion of ethanol and ethylene to liquid and aromatic hydrocarbons, including the conversion of ethanol to ethylene. U.S. Pat. No. 4,727,214 relates to a process for converting anhydrous or aqueous ethanol into ethylene wherein at least one catalyst of the crystalline zeolite type is used, said catalyst having, on the one hand, channels or pores formed by cycles or rings of oxygen atoms having 8 and/or 10 elements or members. U.S. Pat. No. 4,847,223 describes a catalyst comprising from 0.5 to 7% by weight of trifluoromethanesulfonic acid incorporated onto an acid-form pentasil zeolite having a Si/Al atomic ratio ranging from 5 to 54 and a process for producing the same. Also within the scope of said prior art is a process for the conversion of dilute aqueous ethanol to ethylene. U.S. Pat. No. 4,873,392 describes a process for converting diluted ethanol to ethylene which comprises heating an ethanol-containing fermentation broth thereby to vaporize a mixture of ethanol and water and contacting said vaporized mixture with a ZSM-5 zeolite catalyst.

Nitriles are present in trace quantities in olefinic hydrocarbon fractions produced in a refinery, as there are FCC and visbreakers. These nitriles tend to concentrate in the more polar stream as there is the methanol stream in an MTBE unit. The unconverted methanol enriched with nitriles is recycled back to the etherification reactor and results in enhanced poisoning of the acid etherification catalyst.

WO1997045392 provides an improved etherification process that reduces the amount of acidic ion-exchange resin catalyst that is deactivated by nitriles. This process uses a water phase to remove nitriles from a hydrocarbon phase followed by an alcohol phase to remove the nitriles from the water phase. A hydrogenation catalyst is used to convert the nitriles to amines so that they can be more easily removed from the alcohol phase.

EP 1176132 relates to a process for the etherification of olefins comprising:
  bringing into contact, in a reaction zone in which is present a catalyst of the acid type and in which prevail conditions suitable for an etherification reaction, at least one alcohol and a hydrocarbon charge rich in light olefins but containing nitrogen-containing compounds which are accountable to deactivate the catalyst;
  separating the effluents from the reaction zone so as to obtain at least one first fraction rich in ether and a second fraction containing the major portion of the residual alcohol and nitrogen-containing compounds;
  and recycling the second fraction to the inlet of the reaction zone;
said process being characterised in that, prior to it being recycled into the reaction zone, the second fraction undergoes a treatment comprising at least one step of being brought into contact with an acid adsorbent material so as to lower by at least 50% its concentration of said nitrogen-containing compounds.

Advantageously the acid adsorbent material is chosen from the group formed by:
  microporous alumina-silicates, such as the silicalites, the mordenites, the X zeolites and, preferably, the Y zeolites,
  macroreticular resins grafted with acid groups (for example, sulphonic acid),
  silica impregnated with acid (for example, phosphoric acid or sulphuric acid),
  activated carbon, unmodified or impregnated with acid (for example, phosphoric acid or sulphuric acid),
  activated alumina;
  clays, unmodified or treated with an acid,
  molecular sieves,
  crystalline and microporous aluminophosphates,
  mesoporous alumino-silicas.

Advantageously, prior to it being brought into contact with an acid adsorbent material, the second fraction is subjected to a hydrogenation phase selective for the nitrogen-containing compounds which it contains.

These two above prior arts relate only to an etherification process, concern only the removal of the nitriles components that originate from the olefinic hydrocarbon streams and relate only to methanol in which the nitriles concentrate.

The use of alcohols coming from the biomass is of high interest. The use of raw alcohols is of interest to save the expensive steps of further distillation, dewatering by adsorption or purification. As regards the dehydration, it is made in the presence of a catalyst such as alumina or silica-alumina. Such process works well with a substantially pure ethanol such as an ethanol coming from a distillation step or dewatering step over molecular sieves by adsorption, but said distillation or adsorption step requires a lot of energy. On the other hand the use of a raw ethanol leads to a poisoning of acidic catalyst. It has been discovered that the raw ethanol contains impurities which are poisons to the dehydration catalyst or etherification catalyst.

The present invention relates in one embodiment to a purification process of the raw alcohol which doesn't require a lot of energy and prevents the poisoning of the dehydration catalyst.

BRIEF SUMMARY OF THE INVENTION

The present invention is a process for the purification of an alcohol in the course of a process comprising
(1) providing a reaction zone (C) comprising an acid type catalyst;
(2) providing a reaction zone (B) comprising an sorbent material or a combination of sorbents material;
(3) providing an alcohol stream comprising impurities;
(4) introducing the alcohol stream of (3) into the reaction zone (B) and bringing said stream into contact with the adsorbent material at conditions effective to reduce the amount of impurities having an adverse effect on the acid type catalyst of the reaction zone (C);
(5) recovering from step (4) an alcohol stream and introducing it into the reaction zone (C);
(6) optionally introducing one or more reactants (R) into the reaction zone (C);
(7) operating said reaction zone (C) at conditions effective to recover a valuable effluent.

According to an embodiment the impurities are selected in the group consisting of: nitriles, aldehydes, ketons, carboxylic acids, carboxylic esters, amides and the corresponding thio-compounds, and imines.

According to a specific embodiment the impurities are selected in the group consisting of:

in which R is a hydrocarbyl moiety or hydrogen (example are nitriles),
and

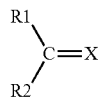

In which X is oxygen, sulphur and R1 is a hydrocarbyl moiety and R2 is a hydrocarbyl moiety, hydrogen, hydroxyl moiety, amine moiety or an alcoxy moiety (examples are aldehydes, ketons, carboxylic acids, carboxylic esters, amides and the corresponding thio-compounds).
and

in which R1 is a hydrocarbyl moiety or hydrogen and R2 is a hydrocarbyl moiety, hydrogen, hydroxyl moiety or an alcoxy moiety (examples are imines)

According to an embodiment only a portion of the alcohol stream of step (3) is treated in step (4), mixed with the untreated portion and introduced into the reaction zone (C).

According to an embodiment, before step (4), the alcohol stream of step (3) is introduced into a reaction zone (A) comprising an hydrogenation catalyst and brought into contact with said catalyst, in the presence of hydrogen, at conditions effective (i) to convert a portion or the whole impurities to modified impurities capable to be retained on the acidic adsorbent material of the reaction zone (B) or (ii) to convert a portion or the whole impurities to modified impurities having no adverse effect on the acid type catalyst of the reaction zone (C) or both (i)+(ii). According to an embodiment only a portion of the alcohol stream of step (3) is treated in the reaction zone (A), mixed with the untreated portion and introduced into the reaction zone (B).

According to an embodiment the acidic adsorbent material in the reaction zone (B) works also as an hydrogenation catalyst. By way of example it is an resin of the Amberlyst® type, USY (ultra-stable zeolite Y) or mesoporous silica-alumina's impregnated with Pd, Pt, Co, Mo or Ni. It means that there is no zone (A) and that in said zone (B) the alcohol stream is brought into contact with said catalyst, in the presence of hydrogen, at conditions effective (i) to convert a portion or the whole impurities to modified impurities capable to be retained on said catalyst of the reaction zone (B) or (ii) to convert a portion or the whole impurities to modified impurities having no adverse effect on the acid type catalyst of the reaction zone (C) or both (i)+(ii). According to an embodiment only a portion of the alcohol stream of step (3) is treated in the reaction zone (B), mixed with the untreated portion and introduced into the reaction zone (C).

According to an embodiment the reaction zone (C) provides the dehydration of an alcohol.

According to an embodiment the reaction zone (C) provides the etherification of an olefin, the reactant (R) of step (6) is the said olefin.

According to an embodiment the reaction zone (C) provides the self-etherification of an alcohol.

Without willing to be bound to any theory, it is believed that N-atoms, linked to C-atoms by means of double or triple bonds are easily hydrolysed in presence of water or alcohols to produce amines, ammonia or ammonium cations that neutralised the acidic catalyst used in reaction zone (C) and it is believed that O-atoms or S-atoms, linked to C-atoms by means of double bonds are easily converted by condensation reactions hence making heavier organic compounds that subsequently result in deposition of coke-like compounds on the surface of the acidic catalyst of reaction zone (C). The hydrogenation step in reaction zone (A) converts the double bonds, existing between N and C, O and C or S and C into the corresponding single bonds (amines, hydroxyl moiety, alcoxy moiety, thiol or thiocarbyl moieties or corresponding decomposition products). The basic amines are subsequently adsorbed on the acid adsorbent material in reaction zone (B) whereas the other hydrogenated compounds with hydroxyl, alcoxy moieties or thiol or thiocarbyl moieties have no adverse effect anymore on the acid catalyst used in reaction zone (C).

DETAILED DESCRIPTION OF THE INVENTION

As regards the adsorbent material of the reaction zone (B), it can be chosen from the group formed by:

microporous alumino-silicates, such as the silicalites, the mordenites, the X zeolites and, preferably, the Y zeolites, macroreticular resins grafted with acid groups (for example, sulphonic acid), strongly acidic ion-exchange resins having the ability to echange anions (for example, macromaticular resions grafted with quaternary amines)

silica impregnated with acid (for example, phosphoric acid or sulphuric acid), activated carbon, unmodified or impregnated with acid (for example, phosphoric acid or sulphuric acid), activated alumina;

clays, unmodified or treated with an acid, molecular sieves, crystalline and microporous aluminophosphates, mesoporous alumino-silicas.

The acidic adsorbent material of the reaction zone (B) can be either one of the above mentioned solides or also a combination of the above.

The above acidic adsorbents can be easily regenerated by heating at about 400° C. or by ion-exchange with acidic aqueous solutions.

As regards the alcohol stream and the dehydration process, the alcohol is any alcohol provided it can be dehydrated to the corresponding olefin. By way of example mention may be made of alcohols having from 2 to 10 carbon atoms. Advantageously the invention is of interest for ethanol, propanol, butanol and phenylethanol. The alcohol stream can comprise an inert component. The inert component is any component provided there is no adverse effect on the dehydration catalyst. Because the dehydration is endothermic the inert component can be used to bring energy. By way of examples the inert component is selected among the saturated hydrocarbons having up to 10 carbon atoms, naphtenes, nitrogen, water and $CO_2$.

As regards the alcohol stream and other process, it can be ethanol, methanol, t-amyl alcohol.

As regards the impurities, ammonia and amines can be adsorbed on the adsorbent of the reaction zone (B). The nitriles (e.g. acetonitrile) need to be hydrogenated to be converted to modified impurities capable to be adsorbed. The aldehydes, ketons, carboxylic acids and esters are hydrogenated to species which have no adverse effect on the catalyst of the reaction zone (C).

As regards the hydrogenation catalyst of the reaction zone (A), it is known per se. One can cite Pt, Pd, Ni, Co, Mo and mixtures to them on any carrier such as carbon, zeolites, molecular sieves, silica or alumina. Advantageously it is Pd on carbon or activated carbon. Such catalysts are described in EP 1176132, the content of which is incorporated in the present invention.

The hydrogenation steps is carried out at a reaction temperature between 0 and 200° C., at a pressure between 1 and 100 bars and a $H_2$ to nitrogen ratio of 1 to 1000 mole/N-atom and a $H_2$ to carbonyl or thionyl ratio of 1 to 1000 mole/O or S-atom.

As regards the reaction zone (C) and the etherification catalyst, is known per se. Etherification with alcohols with 2 or more carbons can be carried out over acidic sulfonated macroporous organic ion exchange resins in the liquid phase at reaction temperature of 30 to 120° C. The reaction can be carried out in conventional fixed bed reactors, fluidized bed liquid phase reactors or in catalytic distillation columns, containing a zone with the acid catalyst.

As regards the reaction zone (C) and the dehydration catalyst, the reaction zone can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The dehydration process to be performed continuously in two parallel "swing" reactors wherein when one reactor is operating, the other reactor is undergoing catalyst regeneration. The dehydration of an alcohol is known per se. As regards the catalyst, it can be any acid catalyst capable to cause the dehydration of ethanol under above said conditions. By way of example, zeolites, modified zeolites, silica-alumina, alumina, silico-alumo-phosphates can be cited. Examples of such catalysts are cited in the above prior art.

According to a first advantageous embodiment the dehydration catalyst is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MIT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst is a crystalline silicate having a ratio Si/Al of at least about 100 or a dealuminated crystalline silicate.

The crystalline silicate having a ratio Si/Al of at least about 100 is advantageously selected among the MFI and the MEL.

The crystalline silicate having a ratio Si/Al of at least about 100 and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching. The crystalline silicate having a ratio Si/Al of at least about 100 can be synthetized as such or it can be prepared by dealumination of a crystalline silicate at conditions effective to obtain a ratio Si/Al of at least about 100. Such dealumination is advantageously made by a steaming optionally followed by a leaching.

The three-letter designations "MFI" and "MEL" each representing a particular crystalline silicate structure type as established by the Structure Commission of the International Zeolite Association.

Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X may be trivalent (e.g. Al, B, . . . ) or tetravalent (e.g. Ge, Si, . . . ). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In this specification, the term "silicon/aluminium atomic ratio" or "silicon/aluminium ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

In a specific embodiment the catalyst preferably has a high silicon/aluminium atomic ratio, of at least about 100, preferably greater than about 150, more preferably greater than about 200, whereby the catalyst has relatively low acidity. The acidity of the catalyst can be determined by the amount of residual ammonia on the catalyst following contact of the catalyst with ammonia which adsorbs to the acid sites on the catalyst with subsequent ammonium desorption elevated temperature measured by differential thermogravimetric analysis. Preferably, the silicon/aluminium ratio (Si/Al) ranges from about 100 to about 1000, most preferably from about 200 to about 1000. Such catalysts are known per se.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a more specific embodiment the crystalline silicate catalyst is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. The catalyst having a high silicon/aluminium atomic ratio for use in the catalytic process of the present invention is manufactured by removing aluminium from a commercially available crystalline silicate. By way of example a typical commercially available silicalite has a silicon/aluminium atomic ratio of around 120. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed there from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof. In preferred embodiment, the framework silicon/aluminium ratio is increased by this process to a value of from about 150 to 1000, more preferably at least 200.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides such as $ZrO_2$ and/or metals, or gels including mixtures of silica and metal oxides. The binder is preferably alumina-free. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate catalyst are mixed together by a mixing process. In such a process, the binder, for example silica, in the form of a gel is mixed with the crystalline silicate catalyst material and the resultant mixture is extruded into the desired shape, for example cylindic or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours. The binder preferably does not contain any aluminium compounds, such as alumina. This is because as mentioned above the preferred catalyst for use in the invention is de-aluminated to increase the silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst.

In addition, the mixing of the catalyst with the binder may be carried out either before or after the steaming and extraction steps.

According to a second advantageous embodiment the dehydration catalyst is a crystalline silicate catalyst having a monoclinic structure, which has been produced by a process comprising providing a crystalline silicate of the MFI-type having a silicon/aluminium atomic ratio lower than 80; treating the crystalline silicate with steam and thereafter leaching aluminium from the zeolite by contact with an aqueous solution of a leachant to provide a silicon/aluminium atomic ratio in the catalyst of at least 180 whereby the catalyst has a monoclinic structure.

Preferably, in the steam treatment step the temperature is from 425 to 870° C., more preferably from 540 to 815° C., and at a water partial pressure of from 13 to 200 kPa.

Preferably, the aluminium is removed by leaching to form an aqueous soluble compound by contacting the zeolite with an aqueous solution of a complexing agent for aluminium which tends to form a soluble complex with alumina.

In accordance with this preferred process for producing monoclinic crystalline silicate, the starting crystalline silicate catalyst of the MFI-type has an orthorhombic symmetry and a relatively low silicon/aluminium atomic ratio which can have been synthesized without any organic template molecule and the final crystalline silicate catalyst has a relatively high silicon/aluminium atomic ratio and monoclinic symmetry as a result of the successive steam treatment and aluminium removal. After the aluminium removal step, the crystalline silicate may be ion exchanged with ammonium ions. It is known in the art that such MFI-type crystalline silicates exhibiting orthorhombic symmetry are in the space group Pnma. The x-ray diffraction diagram of such an orthorhombic structure has one peak at d=around 0.365 nm, d=around 0.305 nm and d=around 0.300 nm (see EP-A-0146524).

The starting crystalline silicate has a silicon/aluminium atomic ratio lower than 80. A typical ZSM-5 catalyst has 3.08 wt % $Al_2O_3$, 0.062 wt % $Na_2O$, and is 100% orthorhombic. Such a catalyst has a silicon/aluminium atomic ratio of 26.9.

The steam treatment step is carried out as explained above. The steam treatment tends to reduce the amount of tetrahedral aluminium in the crystalline silicate framework by forming alumina. The aluminium leaching or extraction step is carried out as explained above. In the aluminium leaching step, the crystalline silicate is immersed in the acidic solution or a solution containing the complexing agent and is then preferably heated, for example heated at reflux conditions (at boiling temperature with total return of condensed vapours), for an extended period of time, for example 18 hours. Following the aluminium leaching step, the crystalline silicate is subsequently washed, for example with distilled water, and then dried, preferably at an elevated temperature, for example around 110° C. Optionally, the crystalline silicate is subjected to ion exchange with ammonium ions, for example by immersing the crystallin silicate in an aqueous solution of $NH_4Cl$.

Finally, the catalyst is calcined at an elevated temperature, for example at a temperature of at least 400° C. The calcination period is typically around 3 hours.

The resultant crystalline silicate has monoclinic symmetry, being in the space group $P2_1/n$. The x-ray diffraction diagram of the monoclinic structure exhibits three doublets at d=around 0.36, 0.31 and 0.19 nm. The presence of such doublets is unique for monoclinic symmetry. More particularly, the doublet at d=around 0.36, comprises two peaks, one at d=0.362 nm and one at d 0.365 nm. In contrast, the orthorhombic structure has a single peak at d=0.365 nm.

The presence of a monoclinic structure can be quantified by comparing the x-ray diffraction line intensity at d=around 0.36 nm. When mixtures of MFI crystalline silicates with pure orthorhombic and pure monoclinic structure are prepared, the composition of the mixtures can be expressed as a monoclinicity index (in %). The x-ray diffraction patterns are recorded and the peak height at d=0.362 nm for monoclinicity and d=0.365 nm for orthorhombicity is measured and are denoted as Im and Io respectively. A linear regression line between the monoclinicity index and the Im/Io gives the relation needed to measure the monoclinicity of unknown samples. Thus the monoclinicity index $\% = (a \times Im/Io - b) \times 100$, where a and b are regression parameters.

The such monoclinic crystalline silicate can be produced having a relatively high silicon/aluminium atomic ratio of at least 100, preferably greater than about 200 preferentially without using an organic template molecule during the crystallisation step. Furthermore, the crystallite size of the monoclinic crystalline silicate can be kept relatively low, typically less than 1 micron, more typically around 0.5 microns, since the starting crystalline silicate has low crystallite size which is not increased by the subsequent process steps. Accordingly, since the crystallite size can be kept relatively small, this can yield a corresponding increase in the activity of the catalyst. This is an advantage over known monoclinic crystalline silicate catalysts where typically the crystallite size is greater than 1 micron as they are produced in presence of an organic template molecule and directly having a high Si/Al ratio which inherently results in larger crystallites sizes.

According to a third advantageous embodiment the dehydration catalyst is a P-modified zeolite (Phosphorus-modified zeolite). Said phosphorus modified molecular sieves can be prepared based on MFI, MOR, MEL, clinoptilolite or FER crystalline aluminosilicate molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
  selecting a zeolite (advantageously with Si/Al ratio between 4 and 500) among $H^+$ or $NH_4^+$-form of MFI, MEL, FER, MOR, clinoptilolite;
  introducing P at conditions effective to introduce advantageously at least 0.05 wt % of P;
  separation of the solid from the liquid if any;
  an optional washing step or an optional drying step or an optional drying step followed by a washing step;
  a calcination step; the catalyst of the XTO and the catalyst of the OCP being the same or different.

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. Nos. 3,911,041, 5,573,990 and 6,797,851.

The catalyst (A1) made of a P-modified zeolite can be the P-modified zeolite itself or it can be the P-modified zeolite formulated into a catalyst by combining with other materials that provide additional hardness or catalytic activity to the finished catalyst product.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering. Final calcination step is performed advantageously at the temperature 400-700° C. either in a static condition or in a gas flow. Air, nitrogen or any inert gases can be used.

According to a specific embodiment of this third advantageous embodiment of the invention the phosphorous modified zeolite is made by a process comprising in that order:
  selecting a zeolite (advantageously with Si/Al ratio between 4 and 500, from 4 to 30 in a specific embodiment) among $H^+$ or $NH_4^+$-form of MFI, MEL, FER, MOR, clinoptilolite;
  steaming at a temperature ranging from 400 to 870° C. for 0.01-200 h
  leaching with an aqueous acid solution at conditions effective to remove a substantial part of Al from the zeolite;
  introducing P with an aqueous solution containing the source of P at conditions effective to introduce advantageously at least 0.05 wt % of P;
  separation of the solid from the liquid;
  an optional washing step or an optional drying step or an optional drying step followed by a washing step;
  a calcination step.

Optionally between the steaming step and the leaching step there is an intermediate step such as, by way of example, contact with silica powder and drying.

Advantageously the selected MFI, MEL, FER, MOR, clinoptilolite (or $H^+$ or $NH_4^+$-form MFI, MEL, FER, MOR, clinoptilolite) has an initial atomic ratio Si/Al of 100 or lower and from 4 to 30 in a specific embodiment. The conversion to the $H^+$ or $NH_4^+$-form is known per se and is described in U.S. Pat. Nos. 3,911,041 and 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphoric acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

EXAMPLES

Raw Bio-Ethanol Analysis

TABLE 1

Main characteristics of raw bio-ethanol

|  |  | Raw ethanol |
|---|---|---|
| Tot S | Mg/l | <0.25 |
| Tot N | mg/l | 20 |
| Basic volatile N | mg/kg | 5 |
| Na | Mg/l | 0.7 |
| Ca | Mg/l | 1.12 |
| Mn | Mg/l | <0.03 |
| Fe | Mg/l | <0.04 |
| Cu | Mg/l | 0.1 |
| Zn | Mg/l | 0.04 |
| Alcohol content | % vol @ 20° C. | 93 |

TABLE 1-continued

Main characteristics of raw bio-ethanol

|  |  | Raw ethanol |
|---|---|---|
| Total acidity | g/hl acetic acid | 0.37 |
| Esters | g/hl | 14.2 |
| Acetaldehyde/Acetal | g/hl | 30 |

From GC-MS analysis, it has been determined that acetonitrile was present as N compound in the raw bio-ethanol feed.

Example 1

Made without any Purification of the Ethanol

The dehydration catalyst is a commercially available silicalite (S115 from UOP, Si/Al=150) which had been subjected to a dealumination treatment by combination of steaming with acid treatment so as provide Si/Al ratio 270. Then the dealuminated zeolite was extruded with silica as binder to have 70% of zeolite in the granule. A detailed procedure of catalyst preparation is described in EP 1194502 B1 (Example I).

FIG. 1 and Table 2 clearly show a very quick deactivation of the catalyst with TOS (Time of Stream) when processing raw bio-ethanol: after 7 hours of run, $C_2^=$ yield drops suddenly.

After regeneration, activity is completely recovered when using ethanol of high purity:

Indeed, Table 3 reports catalyst activity when processing ethanol of high purity, before processing raw bio-ethanol Table 4 reports catalyst activity when processing ethanol of high purity after having processed raw ethanol and having regenerated the catalyst.

The comparison of Table 3 and 4 clearly shows very similar catalyst performances.

Therefore, it indicates that catalyst deactivation is not irreversible. The origin of the catalyst deactivation may be due to compounds selectively reacting with catalyst acid sites.

TABLE 2

Product selectivity for raw bio-ethanol conversion on catalyst

| FEED | EtOH/H2O (95/5) % wt | | | | | | | |
|---|---|---|---|---|---|---|---|---|
| P (bara) | 2 | 2 | 2 | 2 | 2 | 2 | 2 | 2 |
| T (° C.) | 380 | 380 | 380 | 380 | 380 | 380 | 380 | 380 |
| WHSV (H-1) | 7 | 7 | 7 | 7 | 7 | 7 | 7 | 7 |
| EtOH conversion (% wt CH2) | 99.9 | 95.3 | 90.6 | 87.3 | 81.1 | 88.8 | 75.0 | 56.0 |
| DEE | 0.2 | 1.7 | 5.3 | 10.3 | 19.9 | 8.0 | 29.6 | 38.7 |
| Acetaldyde | 0.2 | 0.5 | 0.5 | 0.6 | 0.5 | 0.7 | 0.6 | 0.5 |
| Yield on C-basis (% wt CH2) | | | | | | | | |
| CH4 | 0.0 | 0.0 | 0.0 | 0.0 | 0.0 | 0.0 | 0.0 | 0.0 |
| C2 | 0.4 | 02 | 0.2 | 0.2 | 0.2 | 0.4 | 0.2 | 0.1 |
| C2= | 93.9 | 91.0 | 83.0 | 74.6 | 59.0 | 77.8 | 43.6 | 16.2 |
| C3= | 1.3 | 0.2 | 0.1 | 0.1 | 0.1 | 0.2 | 0.1 | 0.1 |
| C4+ olef | 2.3 | 1.0 | 0.9 | 0.8 | 0.6 | 1.1 | 0.4 | 0.2 |
| C4+ paraf | 0.9 | 0.2 | 0.1 | 0.1 | 0.1 | 0.2 | 0.2 | 0.1 |
| Aromatics | 0.2 | 0.0 | 0.0 | 0.0 | 0.0 | 0.0 | 0.0 | 0.0 |
| Unknown | 0.5 | 0.5 | 0.4 | 0.4 | 0.6 | 0.5 | 0.3 | 0.1 |
| Selectivity on C-basis (% wt CH2) | | | | | | | | |
| CH4 | 0.0 | 0.0 | 0.0 | 0.0 | 0.0 | 0.0 | 0.0 | 0.0 |
| C2 | 0.4 | 0.3 | 0.3 | 0.3 | 0.2 | 0.4 | 0.3 | 0.2 |
| C2= | 94.0 | 95.4 | 91.7 | 85.4 | 72.7 | 87.7 | 58.1 | 28.8 |
| C3= | 1.3 | 0.2 | 0.2 | 0.2 | 0.2 | 0.2 | 0.2 | 0.2 |
| C4+ olef | 2.3 | 1.1 | 1.0 | 1.0 | 0.7 | 1.2 | 0.6 | 0.4 |
| C4+ paraf | 0.9 | 0.2 | 0.1 | 0.2 | 0.1 | 0.2 | 0.2 | 0.3 |
| Aromatics | 0.2 | 0.0 | 0.0 | 0.0 | 0.0 | 0.0 | 0.0 | 0.0 |
| Unknown | 0.5 | 0.5 | 0.4 | 0.5 | 0.8 | 0.6 | 0.5 | 0.2 |
| C2's purity (%) | 99.63 | 99.73 | 99.72 | 99.68 | 99.67 | 99.54 | 99.53 | 99.21 |

TABLE 3

Catalytic performances of catalyst before processing raw bio-ethanol

| P (bara) | FEED EtOH/H2O (95/5)% wt<br>2 |
|---|---|
| T (° C.) | 380 |
| WHSV (H-1) | 7 |
| EtOH conversion (% wt CH2) | 99.95 |
| DEE | 0.1 |
| Acetaldyde | 0.25 |
| Yield on C-basis (% wt CH2) | |
| CH4 | 0.0 |
| C2 | 0.1 |
| C2= | 96.1 |
| C3= | 0.7 |
| C4+ olef | 2.1 |
| C4+ paraf | 0.3 |
| Aromatics | 0.1 |
| Unknown | 0.1 |
| Selectivity on C-basis (% wt CH2) | |
| CH4 | 0.0 |
| C2 | 0.10 |
| C2= | 96.1 |
| C3= | 0.7 |
| C4+ olef | 2.1 |
| C4+ paraf | 0.3 |
| Aromatics | 0.1 |
| Unknown | 0.1 |
| C2's purity (%) | 99.90 |

TABLE 4

Catalytic performances of catalyst after having processed raw bio-ethanol and having regenerated the catalyst

| | FEED EtOH/H2O (95/5)% wt | |
|---|---|---|
| P (bara) | 1.35 | 2 |
| T (° C.) | 380 | 380 |
| WHSV (H-1) | 7 | 7 |
| EtOH conversion (% wt CH2) | 100 | 100 |
| DEE | 0.0 | 0.0 |
| Acetaldyde | 0.39 | 0.26 |
| Yield on C-basis (% wt CH2) | | |
| CH4 | 0.0 | 0.0 |
| C2 | 0.23 | 0.22 |
| C2= | 96.4 | 96.0 |
| C3= | 0.4 | 0.5 |
| C4+ olef | 1.5 | 1.9 |
| C4+ paraf | 0.2 | 0.3 |
| Aromatics | 0.1 | 0.0 |
| Unknown | 0.7 | 0.6 |
| Selectivity on C-basis (% wt CH2) | | |
| CH4 | 0.0 | 0.0 |
| C2 | 0.23 | 0.22 |
| C2= | 96.4 | 96.1 |
| C3= | 0.4 | 0.5 |
| C4+ olef | 1.5 | 1.9 |
| C4+ paraf | 0.2 | 0.3 |
| Aromatics | 0.1 | 0.0 |
| Unknown | 0.7 | 0.6 |
| C2's purity (%) | 99.76 | 99.77 |

Example 2

Ethanol Dehydration with Upstream Purification According to the Invention.

To remove compounds selectively reacting with catalyst acid sites, an upstream purification step is performed. This purification step comprises:

The hydrogenation of nitrile and aldehyde compounds, thus converting rather amphoteric species into basic organic compounds. This step is achieved on a Ni-based catalyst, in the following operating conditions:

Ni-based catalyst, LHSV (EtOH)=12 h$^{-1}$, H2/EtOH=3.3 Nl/l, at ambient temperature and under 2 bara pressure The obtained basic compounds are then removed by adsorption on an acidic adsorbent in the following conditions:

A15 Wet sulfonic acid resin, LHSV (EtOH)=6 h$^{-1}$, at ambient temperature and pressure.

This purified bio-ethanol is then sent to the dehydration section using a commercially available silicalite (S115 from UOP, Si/Al=150) which had been subjected to a dealumination treatment by combination of steaming with acid treatment so as provide Si/Al ratio 270. Then the dealuminated zeolite was extruded with silica as binder to have 70% of zeolite in the granule. A detailed procedure of catalyst preparation is described in EP 1194502 B1 (Example I).

Figure 2:
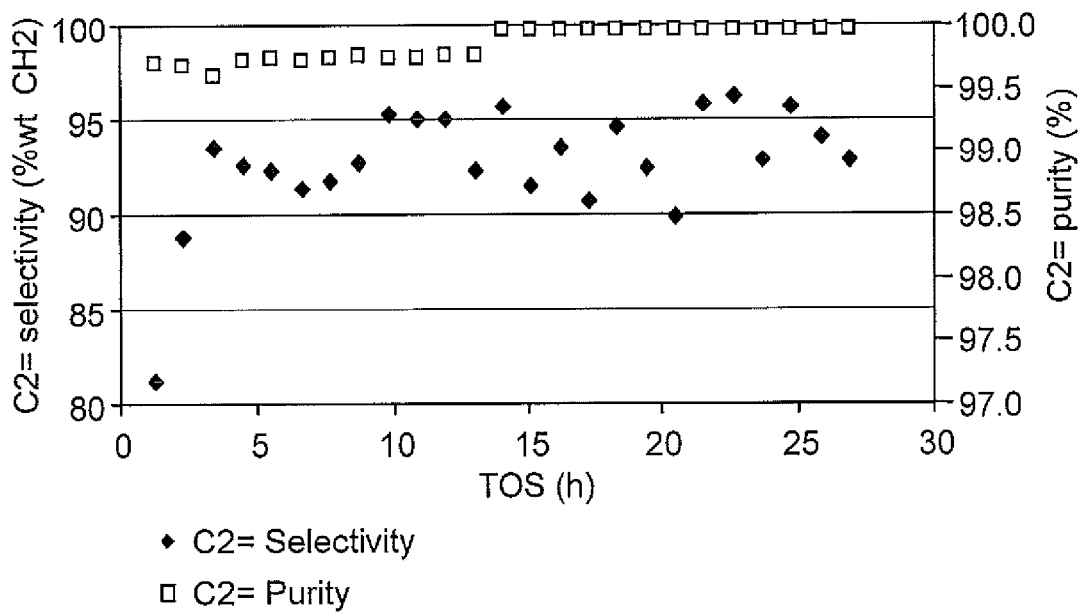
Figure 3:
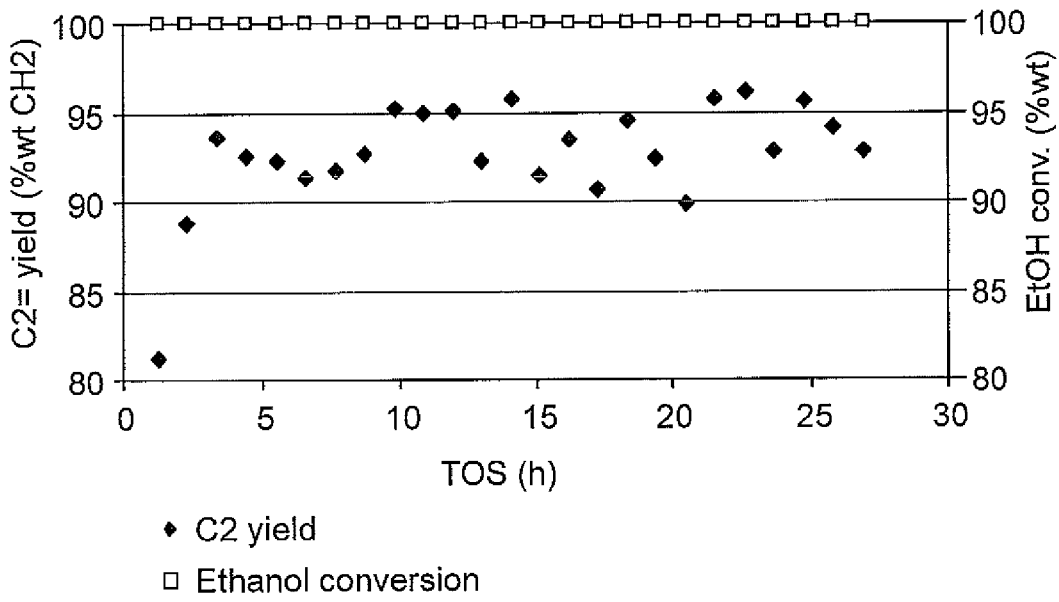

Dehydration operating conditions:

LHSV (EtOH)=7 h$^{-1}$, EtOH/H$_2$O mixture of 95/5% wt, 380° C. and 400° C. and under 2 bara pressure Table 5, FIGS. 2 and 3 gather the catalytic performances of the catalyst when processing a raw bio-ethanol purified by an upstream section. It comes out that thanks to this purification treatment, catalyst performances are very close to those obtained with ethanol of high purity.

TABLE 5

Product selectivity and conversion when processing bio-ethanol feed purified by an upstream purification

| | FEED EtOH/H2O (95/5)% wt | |
|---|---|---|
| P (bara) | 2 | |
| T (° C.) | 380 | 400 |
| WHSV (H-1) | 7 | 7 |
| EtOH conversion (% wt CH2) | 100 | 100 |
| DEE | 3.6 | 1.8 |
| Acetaldyde | 0.21 | 0.23 |
| Yield on C-basis (% wt CH2) | | |
| CH4 | 0.0 | 0.0 |
| C2 | 0.26 | 0.24 |
| C2= | 91.8 | 93.5 |
| C3= | 0.8 | 0.9 |
| C4+ olef | 2.1 | 2.3 |
| C4+ paraf | 0.4 | 0.3 |
| Aromatics | 0.1 | 0.1 |
| Unknown | 0.6 | 0.5 |
| Selectivity on C-basis (% wt CH2) | | |
| CH4 | 0.0 | 0.0 |
| C2 | 0.26 | 0.24 |
| C2= | 91.8 | 93.5 |
| C3= | 0.8 | 0.9 |
| C4+ olef | 2.1 | 2.3 |
| C4+ paraf | 0.4 | 0.3 |
| Aromatics | 0.1 | 0.1 |
| Unknown | 0.6 | 0.5 |
| C2's purity (%) | 99.72 | 99.74 |

For following examples (3 and 4), another raw bio-ethanol was used (labelled raw bio-ethanol 2) having the following characteristics:

TABLE 6

Characteristics of raw bio-ethanol 2

|  |  | Raw bio-ethanol 2 |
|---|---|---|
| Total S | ppm | <0.3 |
| Total N | ppm | 0.8 |
| Na | ppm | 0.07 |
| Ca | ppm | 0.05 |
| Zn | ppm | 0.16 |
| Cu | ppm | 0.11 |
| Aldehydes | ppm | 378 |
| Esters | ppm | 105 |
| Higher alcohols | ppm | 1359 |
| Alcohol Content | % vol @ 20° C. | 93.78 |

Example 3

Figure 4:
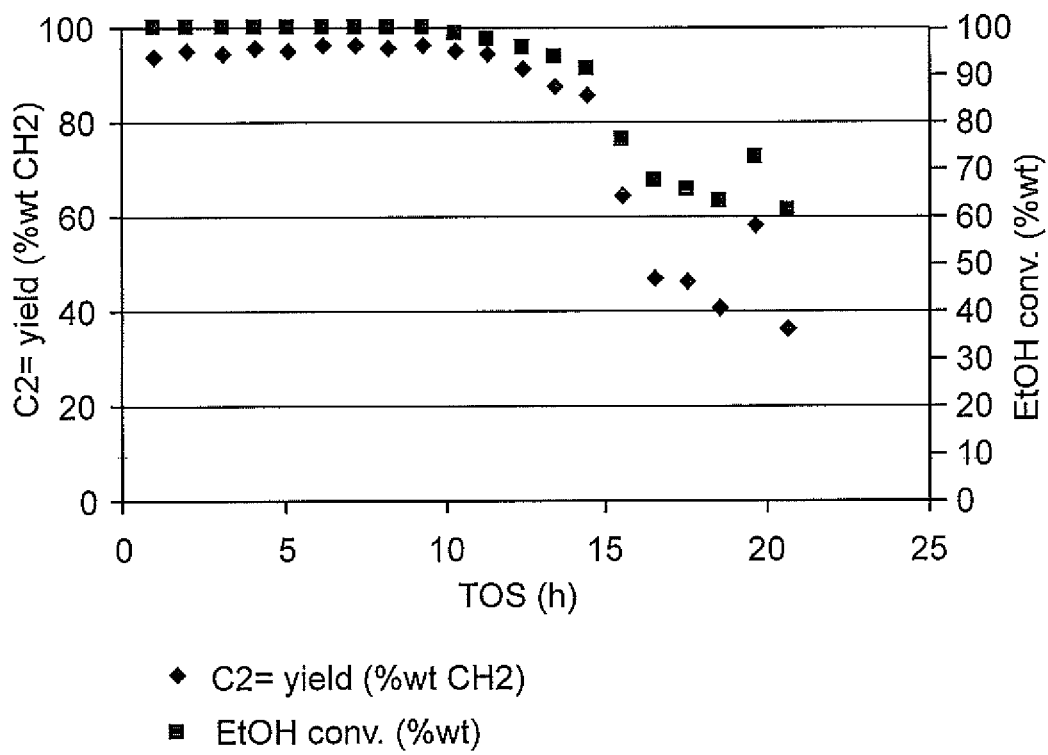

Without ethanol purification section, the catalyst exhibits very quick deactivation: under 2 bara pressure, 400° C., at a LSHV (EtOH) of 7 h−1, and using a mixture of EtOH/H$_2$O of 95/5% wt, the dehydration catalyst starts to deactivate after 10 hours of run. And within 10 hours, ethanol conversion drops from 100% down to 60% wt (C-basis), while C2=yield follows the same trend, going from 96% wt C down to 46% wt C (FIG. 4).

Example 4

This experiment reports the benefit of the use of an improved purification section consisting in:
This purification step comprises:
the hydrogenation of nitrile and aldehyde compounds, thus converting rather amphoteric species into basic organic compounds. This step is achieved on a Ni-based catalyst, in the following operating conditions:
Ni-based catalyst, LHSV (EtOH)=2.4 h$^{-1}$, H$_2$/EtOH=5.6 Nl/l, at ambient temperature and under 15 bara pressure
The obtained basic compounds are then removed by adsorption on an acidic adsorbent in the following conditions:
H—Y zeolitic sorbent (Si/Al of 2.7), LHSV (EtOH)=1.2 h$^{-1}$, at ambient temperature and 15 bara pressure.
the ethanol is then passed through a combination of strongly anionic ion-exchange resin, and strongly acidic ion-exchange resin so as to remove the residual contaminants detrimental to dehydration catalyst activity.

When processing the above purified raw bio-ethanol, the results of the dehydration performed under the following operating conditions:
2 bara pressure, 400° C., at a LSHV (EtOH) of 7 h$^{-1}$, and using a mixture of EtOH/H$_2$O of 95/5% wt
are reported in the table 7.

Very nice catalytic performances are obtained and dehydration catalyst exhibits very good stability along the 120 hours of catalytic test.

TABLE 7

Product selectivity and conversion when processing bio-ethanol feed purified by the improved upstream purification section

|  | FEED EtOH/H2O (95/5)% wt |
|---|---|
| P (bara) | 2 |
| T (° C.) | 400 |
| WHSV (H-1) | 7 |
| EtOH conversion (% wt CH2) | 100 |
| DEE | 0.0 |
| Acetaldyde | 0.01 |
| Yield on C-basis (% wt CH2) | |
| C4 | 0.0 |
| C2 | 0.14 |
| C2= | 96.6 |
| C3= | 0.7 |
| C4+ | 1.7 |
| Aromatics | 0.0 |
| Selectivity on C-basis (% wt CH2) | |
| CH4 | 0.0 |
| C2 | 0.14 |
| C2= | 96.6 |
| C3= | 0.7 |
| C4+ | 1.7 |
| Aromatics | 0.0 |
| C2's purity (%) | 99.86 |

What is claimed is:

1. A process for the purification of an alcohol comprising:
   (1) providing a reaction zone (C) comprising an acid type catalyst;
   (2) providing a reaction zone (B) comprising an adsorbent material and/or a combination of sorbent materials;
   (3) providing an alcohol stream comprising impurities;
   (4) introducing the alcohol stream of (3) into the reaction zone (B) and bringing said alcohol stream into contact with the adsorbent material and/or combination of sorbent materials at conditions effective to reduce the amount of impurities having an adverse effect on the acid type catalyst of the reaction zone (C);
   (5) recovering from step (4) an alcohol stream and introducing it into the reaction zone (C);
   (6) introducing one or more reactants (R) into the reaction zone (C);
   (7) operating said reaction zone (C) at conditions effective to recover a valuable effluent;
   wherein, before step (4), the alcohol stream of step (3) is introduced into a reaction zone (A) comprising a hydrogenation catalyst and is brought into contact with said hydrogenation catalyst, in the presence of hydrogen, at conditions effective to:
     (i) to convert a portion of or the whole of the impurities to modified impurities capable to be retained on the acidic adsorbent material and/or a combination of sorbent materials of the reaction zone (B);
     (ii) to convert a portion of or the whole of the impurities to modified impurities having no adverse effect on the acid type catalyst of the reaction zone (C); or
     both (i) and (ii).

2. The process according to claim 1, wherein the impurities are selected in the group consisting of: nitriles, aldehydes, ketones, carboxylic acids, carboxylic esters, amides and the corresponding thio-compounds, and imines.

3. The process according to claim 1, wherein only a portion of the alcohol stream of step (3) is treated in step (4), which is then mixed with the untreated portion and introduced into the reaction zone (C).

4. The process according to claim 1, wherein only a portion of the alcohol stream of step (3) is treated in the reaction zone (A), which is then mixed with the untreated portion and introduced into the reaction zone (B).

5. A process according to claim 1, of an alcohol comprising:
wherein the acidic adsorbent material and/or combination of sorbent materials in the reaction zone (B) works also as an hydrogenation catalyst.

6. The process according to claim 5, wherein there is no zone (A) and that in said zone (B) the alcohol stream is brought into contact with said hydrogenation catalyst, in the presence of hydrogen, at conditions effective: (i) to convert a portion of or the whole of the impurities to modified impurities capable to be retained on said hydrogenation catalyst of the reaction zone (B) or (ii) to convert a portion of or the whole of the impurities to modified impurities having no adverse effect on the acid type catalyst of the reaction zone (C) or both (i) and (ii).

7. The process according to claim 6, wherein only a portion of the alcohol stream of step (3) is treated in the reaction zone (B), which is mixed with the untreated portion and introduced into the reaction zone (C).

8. The process according to claim 1 wherein, the reaction zone (C) provides the dehydration of an alcohol.

9. The process according to claim 1 wherein, the reaction zone (C) provides the etherification of an olefin, and the reactant (R) of step (6) is the said olefin.

10. The process according to claim 1 wherein, the reaction zone (C) provides the self-etherification of an alcohol.

11. The process according to claim 5, wherein the impurities are selected in the group consisting of: nitriles, aldehydes, ketones, carboxylic acids, carboxylic esters, amides and the corresponding thio-compounds, and imines.

12. The process according to claim 5, wherein only a portion of the alcohol stream of step (3) is treated in step (4), which is mixed with the untreated portion and introduced into the reaction zone (C).

13. The process according to claim 5 wherein, the reaction zone (C) provides the dehydration of an alcohol.

14. The process according to claim 5 wherein, the reaction zone (C) provides the etherification of an olefin, and the reactant (R) of step (6) is the said olefin.

15. The process according to claim 5 wherein, the reaction zone (C) provides the self-etherification of an alcohol.

* * * * *